(12) United States Patent
Todd et al.

(10) Patent No.: US 6,261,768 B1
(45) Date of Patent: Jul. 17, 2001

(54) METHOD FOR AMPLIFYING SPECIFIC NUCLEIC ACID SEQUENCES IN THE PRESENCE OF A THERMOSTABLE RESTRICTION ENDONUCLEASE

(75) Inventors: Alison Velyian Todd, Glebe; Caroline Jane Fuery, Carlingford, both of (AU)

(73) Assignee: Johnson & Johnson Research Pty. Limited, New South Wales (AU)

( * ) Notice: Subject to any disclaimer, the term of this patent is extended or adjusted under 35 U.S.C. 154(b) by 0 days.

(21) Appl. No.: 08/930,828

(22) PCT Filed: Apr. 12, 1996

(86) PCT No.: PCT/AU96/00213

§ 371 Date: Jan. 16, 1998

§ 102(e) Date: Jan. 16, 1998

(87) PCT Pub. No.: WO96/32500

PCT Pub. Date: Oct. 17, 1996

(30) Foreign Application Priority Data

Apr. 13, 1995 (AU) .................................................. PN2452

(51) Int. Cl.[7] ............................... C12Q 1/68; C12P 19/34
(52) U.S. Cl. ........................... 435/6; 435/91.2; 435/91.1; 435/91.5
(58) Field of Search .............................. 435/6, 91.2, 91.5, 435/91.1; 935/77.78; 536/24.33

(56) References Cited

U.S. PATENT DOCUMENTS 5,512,441   4/1996   Ronai ........................................ 435/6

FOREIGN PATENT DOCUMENTS

| 10264 | 8/1992 | (AU) . |
| 10699 | 7/1993 | (AU) . |
| 14776 | 10/1995 | (AU) . |
| 0459532 | 12/1991 | (EP) . |
| 0461496 | 12/1991 | (EP) . |
| 0678582 | 10/1995 | (EP) . |
| 9615139 | 5/1996 | (WO) . |

OTHER PUBLICATIONS

Walker et al., "Isothermal in vitro amplification of DNA by a restriction enzyme/DNA polymerase system", *Proc. Natl. Acad Sci.*, 89:392–396, (1992).

Hruban et al., "A Study of 82 Carcinomas Using a Combination of Mutant–Enriched Polymerasa Chain Reaction Analysis and Allele–Specific Oligonucleotide Hydridization", American journal of Pathology, vol. 143, No. 2 pp. 545–553, (1993).

Lin et al., "Mutation Analysis of K–ras Oncogenes in Gastroenterologic Cancer by the Amplified Created Restriction Sites Method", *American Journal of Clinical Pathology*, vol. 100, No. 6, pp. 686–689, (1993).

Singh et al. International Journal of Oncology. 5: 1009–1018, 1994.*
Pourzand et al. Mutation Research. 228:113–121, 1993.*
Kwok et al. Nucleic Acids Research. 18:999–1005, 1990.*
Levi et al. Cancer Research. 51: 3497–3502, 1991.*

* cited by examiner

Primary Examiner—Carla J. Myers
(74) Attorney, Agent, or Firm—Browdy And Neimark

(57) ABSTRACT

The present invention provides a method of detecting a genetic polymorphism in an individual. In one form, the method comprises the following steps: (1) obtaining a sample containing a nucleic acid from the individual; (2) amplifying the nucleic acid sample from step (1) by a process involving thermocycling and primers, the amplification occurring in the presence of a thermostable restriction endonuclease which retains activity during thermocycling, the primers being selected such that they introduce into either the nucleic acid amplified from nucleic acid not including the polymorphism or from nucleic acid including the polymorphism, a sequence recognized by the thermostable restriction endonuclease; and (3) analyzing the product of step (2) to determine the presence of the polymorphism.

26 Claims, No Drawings

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

TATAAACTTG TGGTAGTTGG ACCT    24

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single (D) TOPOLOGY: linear (ii) MOLECULE TYPE: cDNA (xi) SEQUENCE DESCRIPTION: SEQ ID NO:2:

TATAAACTTG TGGTACCTGG AGC                                               23

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CTCATGAAAA TGGTCAGAGA AACC                                              24

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TTTTGTCGAC GAATATGATC C                                                 21

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TATAAACTTG TGGTAGTTGG ACCT                                              24

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TTTTGTCGAC GAATATGATC C                                                 21

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CTGTATCAAA GCTTGGTCCT GGACCAG                                               27

(2) INFORMATION FOR SEQ ID NO:8:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

CTCATGAAAA TGGTCAGAGA AAC                                                   23

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

TAGCTGTATC GTCAAGGCAC TCTT                                                  24

(2) INFORMATION FOR SEQ ID NO:10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

AAATGATTCT GAATTAGCTG TATCGTC                                               27

(2) INFORMATION FOR SEQ ID NO:11:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

GCACCAGTAA TATGCATATT AAAACAAG                                              28

(2) INFORMATION FOR SEQ ID NO:12:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

ACCATCCAGC TGATCCAGAA CCAT                                                  24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TATAAACTTG TGGTAGTTGG ACCT                                        24

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GGATGACTCA TTAAGGCACT CTTGCCTACG CCC                            33

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TCAGCAAAGA CAAGACAGGT A                                            21

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

AGCAATGCCC TCTCAAGA                                                  18

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TATAAACTTG TGGTACCTGG AGC                                        23

(2) INFORMATION FOR SEQ ID NO:18:

(i) SEQUENCE CHARACTERISTICS:

(A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

TTTTGTCGAC GAATATGATC C                                             21

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GAAAATGGTC AGAGAAACC                                                19

(2) INFORMATION FOR SEQ ID NO:20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GACTGAATAT AAACTTGTGG TAGTTGGACC T                                  31

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GGATGACTCA TTTTCGTCCA CAAAATGATT CTGAATTAG                          39

(2) INFORMATION FOR SEQ ID NO:22:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CCNNNNNNNG G                                                        11

(2) INFORMATION FOR SEQ ID NO:23:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GTTGGAGCTG G                                                         11

(2) INFORMATION FOR SEQ ID NO:24:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GGAGCTGGTG G                                                         11

(2) INFORMATION FOR SEQ ID NO:25:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CCAGGAGGAG T                                                         11

(2) INFORMATION FOR SEQ ID NO:26:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CGCCGGCCAG G                                                         11

(2) INFORMATION FOR SEQ ID NO:27:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

ATAGTTCTTG G                                                         11

(2) INFORMATION FOR SEQ ID NO:28:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
CTGAGTGGAG GTCA                                                        14

(2) INFORMATION FOR SEQ ID NO:29:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

TTATAAGAAG G                                                           11

(2) INFORMATION FOR SEQ ID NO:30:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

AAATATCATC TT                                                          12

(2) INFORMATION FOR SEQ ID NO:31:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

AAATATCATT GG                                                          12

(2) INFORMATION FOR SEQ ID NO:32:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

GACCATCGAC G                                                           11

(2) INFORMATION FOR SEQ ID NO:33:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

CCCTGGGCAG G                                                           11
```

METHOD FOR AMPLIFYING SPECIFIC NUCLEIC ACID SEQUENCES IN THE PRESENCE OF A THERMOSTABLE RESTRICTION ENDONUCLEASE

FIELD OF INVENTION

This invention relates to methods for in vitro amplification of specific nucleic acid target sequences. In particular the invention relates to methods which employ thermophilic restriction endonucleases to mediate selective amplification of nucleic acid targets which contain sequence differences including point mutations, deletions and insertions.

BACKGROUND OF THE INVENTION

A variety of inherited and acquired diseases are associated with genetic variations such as point mutations, deletions and insertions. Some of these variants are directly associated with the presence of disease, while others correlate with disease risk and/or prognosis. There are of the order 500 human genetic diseases which result from mutations in single genes. These include cystic fibrosis, muscular dystrophy, α1-antitrypsin deficiency, phenylketonuria, sickle cell anaemia or trait, and various other haemoglobinopathies. Furthermore, individuals with increase susceptibility to several common polygenic conditions, such as atherosclerotic heart disease, have been shown to have an association with the inheritance of a particular DNA sequence polymorphism. Cancer is thought to develop due to accumulation of lesions in genes involved in cellular proliferation or differentiation. The ras proto-oncogenes, K-ras, N-ras, and H-ras, and the p53 tumour suppressor gene are examples of genes which are frequently mutated in human cancers. Specific mutations in these genes leads to activation or increased transforming potential. Genetic analysis is likely to become routine in the clinic for assessing disease risk, diagnosis of disease, predicting a patient's prognosis or response to therapy, and for monitoring a patient's progress. The introduction of such genetic tests depends on the development of simple, inexpensive, and rapid assays for genetic variations.

In rare instances mutations can be detected if they happen to lie within a naturally occurring restriction endonuclease recognition/cleavage site. WO84/01389 describes a method for discriminating between wild type genes and non wild type variants by screening for the presence or absence of restriction endonuclease sites. The inventors demonstrated the principle by analysis of variant sequences at condon 12 of the human H-ras proto-oncogene. The wild sequence at condon 12 forms part of the recognition/cleavage sites for the restriction endonucleases Nae I and Hpa II. Digestion with these endonucleases can discriminate between the wild type proto-oncogene and activated oncogenes which harbour mutations at this condon. Point mutations at condon 12 of H-ras are frequently found in bladder carcinomas and this general strategy form the basis of screening kits for medical diagnosis.

Methods of in vitro nucleic acid amplification have widespread applications in genetics and disease diagnosis. The polymerase chain reaction (PCR) is a powerful, exquisitely sensitive procedure for in vitro amplification of specific segments of nucleic acids (R. K. Saiki, et al 1985 Science 230, 1350–1354 of F. F. Chehab, et al 1987 Nature 329, 293–294 and U.S. Pat. No. 4,683,202 and U.S. Pat. No. 4,683,195 and U.S. Pat No. 4,800,159 and U.S. Pat. No. 4,965,188 and U.S. Pat. No. 5,176,995). The PCR is mediated by oligonucleotide primers that flank the target sequence to be synthesized, and which are complementary to sequences that lie on opposite strands of the template DNA. The steps in the reaction occur as a result of temperature cycling (thermocycling). Template DNA is first denatured by heating, the reaction is then cooled to allow the primers to anneal to the target sequence, and then the primers are extended by DNA polymerase. The cycle of denaturation, annealing and DNA synthesis is repeated many times and the products of each round of amplification serve as templates for subsequent rounds. This process results in the exponential amplification of amplicons which incorporate the oligonucleotide primers at their 5' termini and which contain newly synthesized copies of the sequences located between the primers.

The PCR is extremely versatile and many modifications of the basic protocols have been developed. Primers used for PCR may be perfectly matched to the target sequence or they can contain mismatched and or modified bases. Additional sequences at the 5' end or primers can facilitate capture of PCR amplicons and the inclusion of labelled primers can facilitate detection. The inclusion of mismatched bases within primers can result in the induction of new restriction endonuclease recognition/cleavage sites. These sites can be located completely within the primer sequence. Alternatively, they can span a sequence which lies partially within the primer and partially within the newly synthesized target sequence (J. B. Cohen and A. D. Levinson (1988) Nature 334, 119–124). The general rules for designing primers which contain mismatched bases located near the 3' termini have been established (S. Kwok, et al. (1990) Nucleic Acids Research 18, 999–10005).

Modified primers containing mismatched bases were used to induce novel recognition/cleavage sites for restriction endonucleases in H-ras amplicons which were mutated at codon 12 (R. Kumar and M. Barbacid (1988) oncogene 3, 647–651). Similarly, primers containing mismatched bases were employed in protocols known as allele specific enrichment (Todd A V et al Leukemia, 1991; 5:160) or enriched PCR (Levi S et al Cancer Res., 1991; 6:1079). These are very sensitive protocols for the detection of point mutations. In these protocols, DNA samples were amplified with primers which induced either an Eco NI site in N-ras amplicons, or a Bst NI site in K-ras amplicons, provided the sequences were wild type at condon 12. Aliquots of the PCR reactions were digested with the appropriate restriction endonuclease to cleave wild type amplicons prior to re-amplification of the digestion-resistant amplicons in a second round of the PCR. These protocols resulted in preferential amplification of sequences harbouring point mutations at condon 12 of ras. More recently, a simplified enriched PCR protocol was published which allowed the reaction to be performed in a single tube (Singh et al Int J Oncol., 1994; 5: 1009). This protocol also required an initial round of PCR amplification, however, the restriction endonuclease was then added directly to the reaction tube. Following incubation with the restriction endonuclease, a second round of the PCR resulted in amplification of sequences harbouring mutations within the restriction endonuclease recognition/cleavage site. This analysis of natural or induced restriction endonuclease sites in PCR amplicons requires sequential activity of a DNA polymerase for the PCR, followed by activity of a restriction endonuclease for cleavage analysis. Enriched PCR protocols require sequential activity of firstly a DNA polymerase for the PCR, then restriction endonuclease activity to cleave specific sequences, followed by further DNA polymerase activity to re-amplify digestion resistant amplicons.

The ability to simultaneously exploit the activities of a restriction endonuclease and a DNA polymerase during the PCR could provide several advantages. It could allow the development of simple protocols for exclusive or preferential amplification of variant sequences in reactions which contain all reagents, including enzymes, at the initiation of the PCR. It was not previously known whether or not inclusion of a restriction endonuclease in a PCR could result in (i) complete (or partial) inhibition of amplification of a sequence which contains the recognition/cleavage site for the restriction endonuclease and (ii) exclusive (or preferential) amplification of a variant of this sequence which lacks the recognition/cleavage site for the restriction endonuclease. The ability to completely inhibit amplification of a sequence and/or exclusively amplify a variant sequence could lead to the development of protocols which do not require further manipulation prior to analysis. A reduction in the number of steps required for selective amplification and/or subsequent analysis of amplicons could lead to the development of protocols which are more rapid, less labour intensive and/or more amenable to automation. A further advantage is that reactions would be performed in a closed system and this would reduce the opportunity for contamination during the PCR Such protocols would require concurrent activity of a restriction endonuclease and a DNA polymerase under conditions compatible with the PCR. The restriction endonuclease and the DNA polymerase must i) function in identical reaction conditions (eg., salt, pH) which must be compatible with the PCR and ii) must be sufficiently thermostable in these reaction conditions to retain activity during the thermocycling with is required for the PCR. Restriction endonuclease which are suitable for combination with the PCR must be active at temperatures which are compatible with stringent conditions for annealing of primers during the PCR, typically 50° C.–65° C. Simultaneous activity of thermophilic DNA polymerases and restriction endonucleases has previously been exploited to mediate in vitro amplification in an isothermal reaction known as strand displacement amplification (EP O 684 315 AI). It was not previously known whether restriction endonucleases could be sufficiently thermostable to maintain activity during the thermocycling required for the PCR.

SUMMARY OF INVENTION

In a first aspect the present invention consists in a method of detecting a genetic polymorphism in an individual, the method comprising the following steps:

(1) Obtaining a sample containing nucleic acid from the individual;

(2) Amplifying the nucleic acid sample from step (1) by a process involving thermocycling and primers, the amplification occurring in the presence of a thermostable restriction endonuclease which retains activity during thermocycling, the primers being selected such that they introduce into either the nucleic acid amplified from nucleic acid not including the polymorphism or from nucleic acid including the polymorphism, a sequence recognised by the thermostable restriction endonuclease; and (3) Analysing the product of step (2) to determine the presence or absence of the polymorphism.

In one embodiment of this aspect of the present invention the primers introduce the sequence recognised by the thermostable restriction endonuclease into the nucleic acid amplified from the nucleic acid not including the polymorphism.

In a second aspect the invention consists in a method detecting a genetic polymorphism in an individual, the method comprising the following steps:

(1) Obtaining a sample containing nucleic acid from the individual;

(2) Amplifying the nucleic acid sample from step (1) by a process involving thermocycling and primers, the amplification occurring in the presence of a thermostable restriction endonuclease having concurrent activity, the restriction endonuclease being selected such that it recognises nucleic acid not including the polymorphism but not nucleic acid including the polymorphism or vice versa; and (3) Analysing the product of step (2) to determine the presence of absence of the polymorphism.

In one embodiment of this aspect of the present invention the thermostable restriction endonuclease recognises nucleic acid not including the polymorphism.

In a preferred embodiment of the present invention the method further comprises the following additional steps of:

(4) reacting the amplified nucleic acid from step (2) with at least one restriction endonuclease, the at least one restriction endonuclease being selected such that it digests the amplified nucleic acid including a particular polymorphism; and (5) determining whether digestion occurs in step (4), digestion being indicative of the presence of the particular polymorphism.

There are a number of techniques for amplifying nucleic acid which involve thermocycling. These include polymerase chain reaction (PCR), ligase chain reaction, transcription-based amplification and restriction amplification. It is, however, presently preferred that the process involving thermocycling is PCR.

In yet a further preferred embodiment the step (3) analysis comprises detecting the presence or absence of amplified nucleic acid from step (2), the presence or absence of amplified nucleic acid indicating the presence or absence of the polymorphism.

Whilst the method of the present invention can be used with varying types of nucleic acid typically the nucleic acid will be DNA.

In yet another preferred embodiment of the present invention the thermostable restriction endonuclease is selected from the group consisting of Bst NI, Bsl I, Tru 9I and Tsp 509 I.

The method of the present invention can be used to detect a range of genetic polymorphism including those occurring in one of the ras proto-oncogenes, K-ras, N-ras, and H-ras, or the p53 tumour suppressor gene, or in HIV-I, cystic fibrosis trans-membrane conductance regulator, α-antitrypsin or β-globin. The method of the present invention is particularly useful in detecting polymorphism in codon 12 of K-ras.

The method of the present invention can be used for the analysis of a range of genetic polymorphisms including point mutations, small deletions and insertions. It was discovered that thermostable restriction endonucleases can be sufficiently thermostable to retain activity during thermocycling. It was also found that the PCR can be performed, using various polymerases, under the same buffer conditions which maintain activity and thermostability of the restriction endonucleases. It was discovered that the inclusion of a thermostable restriction endonuclease during the PCR can result in (i) inhibition of amplification of a sequence which contains the recognition/cleavage site for the restriction endonuclease and (ii) exclusive amplification of a variant of this sequence which lacks the recognition/cleavage site for the restriction endonuclease. These discoveries allowed the development of protocols for restriction endonuclease mediated selective PCR (REMS-PCR). REMS-PCR is simpler than other PCR protocols which utilise restriction endonucleases for the analysis of sequence variations. All components of the reaction are present at the initiation of the PCR and no subsequent manipulations are required prior to analysis. The reaction can therefore be performed in a closed vessel or chamber. It was also found that the inclusion of a thermostable restriction endonuclease during PCR can result in (i) partial inhibition of amplification of nucleic acid which contains the recognition/cleavage site for the restriction endonuclease and (ii) preferential amplification of a variant of this sequence which lacks the recognition/cleavage site for the restriction endonuclease.

DETAILED DESCRIPTION OF THE INVENTION

As used herein, the following terms and phases are defined as follows:

The PCR is an in vitro DNA amplification procedure which requires two primers that flank the target sequence to be synthesized. A primer is an oligonucleotide sequence which is capable of hybridising in a sequence specific fashion to the target sequence and extending during the PCR. Amplicons or PCR products or PCR fragments are extension products which comprise the primer and the newly synthesized copies of the target sequences. Multiplex PCR systems contain multiple sets of primers which result in simultaneous production of more than on amplicon. Primers may be perfectly matched to the target sequence or they may contain internal mismatched bases which can result in the induction of restriction endonuclease recognition/cleavage sites in specific target sequences. Primers may also contain additional sequences and/or modified or labelled nucleotides to facilitate capture or detection of amplicons. Repeated cycles of heat denaturation of the DNA, annealing of primers to their complementary sequences and extension of the annealed primers with DNA polymerase result in exponential amplification of the target sequence. The terms target or target sequence refer to nucleic acid sequences which are amplified. The term template refers to the original nucleic acid which is to be amplified.

Restriction endonuclease mediated selective PCR (REMS-PCR) is an assay developed by the present inventor which applies the method of the present invention. This assay requires simultaneous activity of a restriction endonuclease and a DNA polymerase during the PCR. Restriction endonucleases which are suitable for REMS-PCR are preferably active at temperatures which are compatible with stringent conditions for annealing of oligonucleotide primers during the PCR, typically 50° C.–65° C. A selection of commercially available restriction endonucleases which have high optimal incubation temperatures in this range are listed below in Table 1.

The term "individual" is used in herein in broadest sense and is intended to cover human and non-human animals, bacteria, yeast, fungi and viruses.

TABLE 1

| Restriction Endonuclease | Recognition/Cleavage Sequence | Optimal Incubation Temperature (s) |
|---|---|---|
| Acc III | TCCGGA | 65° C. |
| Acs I/Apo I | (A/G)AATT(T/C) | 50° C. |
| Acy I | G(A/G)CG(C/T)C | 50° C. |
| Bco I | C(C/T)CG(A/G)G | 65° C. |
| Bsa BI/Bsi BI | GATNNNNATC | 60° C./55° C. |
| Bsa MI | GAATGCN | 65° C. |
| Bsa JI | CCNNGG | 60° C. |
| Bsa OI | CG(A/G)(T/C)CG | 50° C. |
| Bsa WI | (A/T)CCGG(A/T) | 60° C. |
| Bsc BI | GGNNCC | 55° C. |
| Bsc CI | GAATGCN | 65° C. |
| Bsc FI | GATC | 55° C. |
| Bse AI | TCCGGA | 55° C. |
| Bsi CI | TTCGAA | 60° C. |
| Bsi EI | CG(A/G)(C/T)CG | 55° C. |
| Bsi HKAJ | G(A/T)GC(A/T)C | 65° C. |
| Bsi LI | CC(A/T)GG | 60° C. |
| Bsi MI | TCCGGA | 60° C. |
| Bsi QI | TGATCA | 60° C. |
| Bsi WI | CGTACG | 55° C. |
| Bsi XI | ATCGAT | 65° C. |
| Bsi ZI | GGNCC | 60° C. |
| Bsi I | CCNNNNNNNGG | 55° C. |
| Bsm I | GAATGCN | 65° C. |
| Bsm AI | GTCTCN$_1$/N$_5$ | 55° C. |
| Bsm B1 | CGTCTCN$_1$/N$_5$ | 55° C. |
| Bss T11 | CC(A/T)(A/T)GG | 50° C. |
| Bsr 1 | ACTGGN | 65° C. |
| Bsr D1 | GCAATGNN | 60° C. |
| Bsi 711 | GCAGCN$_8$ | 50° C. |
| Bsi B1 | TTCGAA | 65° C. |
| Bsi N1 | CC(A/T)GG | 60° C. |
| Bsi U1 | CGCG | 60° C. |
| Bsi Y1 | (A/G)GATC(C/T) | 60° C. |
| Bsi Z1 | CGGCCG | 50° C. |
| Dsa 1 | CC(A/G)(C/T)GG | 55° C. |
| Mae 11 | ACGT | 55° C. |
| Mae 111 | GTNAC | 55° C. |
| Mwo 1 | GCNNNNNNNGC | 60° C. |

TABLE 1-continued

| Restriction Endonuclease | Recognition/Cleavage Sequence | Optimal Incubation Temperature (s) |
|---|---|---|
| Ssp B1 | TGTACA | 50° C. |
| Taq 1 | TCGA | 65° C. |
| Tfi 1 | GA(A/T)TC | 65° C. |
| Tru 9I | TTAA | 65° C. |
| Tsp 45 1 | GT(C/G)AC | 65° C. |
| Tsp 509 1 | AATT | 65° C. |
| Tsp R 1 | NNCAGTGNN | 65° C. |
| Tth 111I | GACNNNGTC | 65° C. |

A = adenine; G = guanine; T = thymine; C = cytosine; and N = A or G or T or C

In order that the nature of the present invention may be more clearly understood preferred forms thereof will now be described by reference to the following examples.

EXAMPLE 1

Assay for Assessing the Activity/Thermostability of Restriction Endonucleases

The activity/thermostability assay was used to examine the thermostability and residual enzymatic activity of restriction endonucleases including Bst NI, Bsl I, Tru 9I, and Tsp 509 I, in various buffer systems following a defined number of thermocycles.

The activity/thermostability of Bst NI, Bsl I and Tru 9I was compared for a variety of buffer conditions. Reactions contained primers (as indicated below in Table 2), each dNTP, (dATP, dCTP, dTTP, dGTP) at 100 µM, 0.5 units of Taq DNA polymerase (5 units/µl; AmpliTaq; Perkin Elmer) and either 20 units of Bst NI (10 units/µl; New England Biolabs) or Tru 9I (10 units/µl;Boehringer Mannheim) or 10 units of Bsl I (50 units/µl; New England Biolabs) in a total reaction volume of 25 µl.

TABLE 2

| Primer | Amount (pmole) | Present in assay for | Sequence |
|---|---|---|---|
| 5BKIT | 7.5 | Bst NI | TATAAACTTGTGGTAGTTGGACCT(SEQ ID NO:1) |
| 5BKIQ | 7.5 | Bsl 1, Tru 9I | TATAAACTTGTGGTACCTGGAGC(SEQ ID NO:2) |
| 3KiE | 7.5 | Bst NI, Bsl 1, Tru 9I | CTCATGAAAATGGTCAGAGAAACC(SEQ ID NO:3) |
| 5BKIW | 1.25 | Bsl 1 | TTTTGTCGACGAATATGATCC(SEQ ID NO:4) |

In addition, reactions contained one of the following basic buffer systems (set out in Table 3) with or without various additional reagents.

TABLE 3

| Basic Buffer Name<br>*** New England Biolabs<br>** Boehringer Mannhein<br>* Perkin Elmer | Salt | Tris HCl (pH at 25° C.) | MgCl$_2$ mM | DTT mM |
|---|---|---|---|---|
| *** NEB2<br>** SuRE/Cut M | 50 mM NaCl | 10 mM (7.9) | 10 | 1 |
| *** NEB3 | 100 mM NaCl | 50 mM (7.9) | 10 | 1 |
| * PCR Buffer II | 50 mM KCl | 10 mM (8.3) | | |
| * Stoffel Buffer | 10 mM KCl | 10 mM (8.3) | | |
| MTris10 | 50 mM NaCl | 10 mM (8.0 or 8.3 or 8.5 or 8.75) | | |
| Htris50 | 100 mM NaCl | 50 mM (8.0 or 8.3 or 8.5 or 8.75 or 9.0 or 9.5) | | |

The reactions were placed in a GeneAmp PCR system 9600 thermocycler (Perkin Elmer), heated to high temperature and thermocycled as indicated in Table 4.

TABLE 4

| Restriction Endonuclease | Bst N1 | Bsl 1 | Tru 9I |
|---|---|---|---|
| Initial Temperature | 94° C. for 2 min. | 92° C. for 1 min. | 94° C. for 2 min. |
| Thermocycling | 60° C. for 1 min<br>92° C. for 20 sec | 55° C. for 1 min<br>92° C. for 20 sec | 65° C. for 1 min<br>92° C. for 20 sec |
| Number of thermocycles | 15 or 30 | 15 or 30 | 15 or 30 |
| Optimal Incubation Temperature | 60° C. | 55° C. | 55° C. |

Following thermocycling, 8 μg of plasmid DNA in a volume of 5 μl (pGFP-C1; Clontech) was added to each tube and the reactions were incubated for 1 hour at the optimal temperature as indicated by the manufacturer. The ability of the restriction endonuclease to cleave the plasmid DNA was assessed by electrophoresis on 3% Nusieve GTG gel (FMC Bioproducts, Rockland, Md.). The endonuclease was scored as either being inactivated (I); having low (L), moderate (M) or high (H) activity; or having full (F) activity. (Table 5)

TABLE 5

| Basic Buffer | Additional Reagents | Bst NI Activity Cycles | | Bsl I Activity Cycles | | Tru 9I Activity Cycles | |
|---|---|---|---|---|---|---|---|
| | | 15 | 30 | 15 | 30 | 15 | 30 |
| NEB2 | | M | L | | | | |
| SuRE Cut M | | | | | | M | L |
| NEB3 | | F | M | | | | |
| 1 × PCR Buffer II | 3 mM MgCl$_2$ | M | L | | | | |
| | 6 mM MgCl$_2$ | M | L | I | I | | |
| | 10 mM MgCl$_2$ | H | M | I | I | | |
| | 10 mM MgCl$_2$; 1 mM DTT | | | H | M | | |
| 1 × Stoffel Buffer | 3 mM MgCl$_2$ | M | L | | | | |
| | 6 mM MgCl$_2$ | M | L | I | I | | |
| | 10 mM MgCl$_2$ | M | L | I | I | | |
| | 10 mM MgCl$_2$; 1 mM DTT | | | H | M | | |
| MTris 10 pH 8.3 | 10 mM MgCl$_2$ | H | L | I | I | | |
| HTris 50 pH 8.3 | | F | M | | | | |
| MTris 10 pH 8.0 | 10 mM MgCl$_2$; 1 mM DTT | | | | | | |
| MTris 10 pH 8.3 | 10 mM MgCl$_2$; 1 mM DTT | | | H | M | | |
| MTris 10 pH 8.0 | 10 mM MgCl$_2$ | M | L | | | | |
| MTris 10 pH 8.3 | | H | L | I | I | | |
| MTris 10 pH 8.5 | | M | L | I | I | | |
| MTris 10 pH 8.75 | | | | I | I | | |
| | 10 mM MgCl$_2$; 1 mM DTT | | | H | M | H | L |
| HTris 50 pH 8.5 | 6 mM MgCl$_2$ | | | I | I | | |
| HTris 50 pH 8.5 | 6 mM MgCl$_2$; 1 mM DTT | | | H | M | | |
| HTris 50 pH 8.0 | 10 mM MgCl$_2$ | F | M | | | | |
| HTris 50 pH 8.3 | | F | M | I | I | | |
| HTris 50 pH 8.5 | | F | M | I | I | | |
| HTris 50 pH 8.5 | 10 mM MgCl$_2$; 1 mM DTT | | | H | M | H | L |
| HTris 50 pH 8.75 | 10 mM MgCl$_2$ | | | I | I | | |
| | 10 mM MgCl$_2$; 1 mM DTT | | | H | M | H | L |
| HTris 50 pH 8.3 | 3 mM MgCl$_2$ | H | M | | | | |
| | 6 mM MgCl$_2$ | F | M | | | | |
| | 10 mM MgCl$_2$ | F | M | I | I | | |
| HTris 50 pH 8.3 | 10 mM MgCl$_2$; 1 mM DTT | | | H | M | | |
| HTris 50 pH 8.3 | — | F | M | | | | |
| 6 mM MgCl$_2$ | 1 mM DTT | H | M | | | | |
| | 0.1 mg/ml acetylated BSA (aBSA) | H | M | | | | |
| | 0.1 mg/ml non-acetylated BSA (non-a BSA) | H | M | | | | |
| | 1 mM DTT + aBSA | M | M | | | | |
| | 1 mM DTT + non-aBSA | M | L | | | | |
| | 10% glycerol | H | M | | | | |
| HTris 50 pH 9.0 | 10 mM MgCl$_2$; 1 mM DTT | | | | | H | M |
| HTris 50 pH 9.5 | 10 mM MgCl$_2$; 1 mM DTT | | | | | F | M |

These experiments indicated that the activity/thermostability of restriction endonucleases during thermocycling varied considerably depending on both the restriction endonuclease and buffer system in which it was assayed. The pH and ionic strength of the Tris buffer, the choice and concentration of monovalent cation (K$^+$ or Na$^+$), the concentration of free $Mg^{2+}$, and the presence of other additives, particularly DTT, could influence the activity/thermostability. The influence of each of these components could depend on the other components in the buffer. For example, Bst NI retained more activity in PCR Buffer II containing 10 mM $MgCl_2$ than in this buffer containing either 3 or 6 mM $MgCl_2$. In contrast, varying the concentration of $MgCl_2$ between 3 and 10 mM had little effect of Bst NI activity when in HTris 50 (pH 8.3) buffer. In another example, the pH of the buffer had a greater influence on thermostability/activity of Bst NI in MTris 10 than in HTris 50.

Bst NI remains fully active following 15 thermocycles and moderately active following 30 thermocycles in buffer systems which contain either i) 100 mM NaCl, 50 mM Tris HCl (pH 8.3) and 6 mM $MgCl_2$ or ii) 100 mM NaCl, 50 mM Tris HCl (pH 8.0–8.5) and 10 mM $MgCl_2$ or iii) NEB 3 buffer and 0.1 mg/ml. Bst NI is more active in these buffers during thermocycling than in NEB 2 buffer with 0.1 mg/ml acetylated BSA which are the buffer conditions recommended by the manufacturers.

Similar experiments examining activity/thermostability of Bsl I indicated that this endonuclease requires the presence of 1 mM DTT in order to remain active following thermocycling. Provided DTT is present, Bsl I remains active in a broad range of conditions. Bsl I retains moderate activity following 30 thermocycles in buffer systems which contain i) PCR buffer II (Perkin Elmer), 1 mM DTT and 10 mM $MgCl_2$ ii) Stoffel buffer (Perkin Elmer), 1 mM DTT and 10 mM $MgCl_2$ iii) 50 mM NaCl, 10 mM Tris HCl (pH 8.5), 1 mM DTT and 10 mM $MgCl_2$ iv) 100 mM NaCl, 50 mM Tris HCl (pH 8.3–8.5), 1 mM DTT and 10 mM $MgCl_2$ or v) 100 mM NaCl, 50 mM Tris HCl (pH 8.5), 1 mM DTT and 6 mM $MgCl_2$. Tru 9I retains moderate activity following 30 thermocycles in a buffer system which contains 100 mM NaCl, 50 mM Tris HCl (pH 8.5–9.25), 10 mM $MgCl_2$ and 1 mM DTT. Experiments similar to those described above showed that Tsp 509 I retains moderate activity following 30 thermocycles in a buffer system which contains 50 mM NaCl, 10 Tris Hcl (pH 9.0 to 10). 10 mM $MgCl_2$ and 1 mM DTT.

EXAMPLE 2

Identification of Buffer Systems Compatible With Restriction Endonuclease and DNA Polymerase Thermostability/Activity and the PCR The range of buffers which was assessed for ability to maintain thermostability/activity of Bst NI (above) was also assessed for compatibility with the PCR using primers 5BKIT or 5BKIW with 3KiE. The PCR mixtures containing genomic K562 DNA (800 ng), 30 pmole of 5BKIT or 30 pmole 5BKIW, 30 pmole of 3KiE, and each dNTP (dATP, dCTP, dTTP, dGTP) at 100 $\mu$M were set up for various buffer systems. Four units of Taq DNA polymerase (5 units/$\mu$l; AmpliTaq, Perkin Elmer) were mixed with TaqStart™ antibody (0.16 $\mu$l in 3.8 $\mu$l of antibody dilution buffer, Clontech) to give a final molar ratio of Taq DNA polymerase: TaqStart™ antibody of 1:5. The Taq DNA polymerase: TaqStart™ antibody mixture was incubated for 15 min at room temperature prior to addition to the mixtures. The total reaction volumes were 100 $\mu$l. The reactions were placed in a GeneAmp PCR system 9600 (Perkin Elmer), denatured at 94° C. for 2 min and then subjected to 30 cycles of 60° C. for 1 min followed by 92° C. for 20 sec. Reactions were held at 60° C. for 15 min after thermocycling.

A 28 $\mu$l aliquot of each reaction was analysed without subsequent manipulation by electrophoresis on a 5% Nusieve GTG gel (FMC Bioproducts, Rockland, Md.). The gel was photographed using Stratagene Eagle Eye II video system. The efficiency of amplification with primers 5BKIT and 3KiE, or 5BKIW and 3KiE was rated as low, moderate or high. These primers were designed for use in a multiplex REMS-PCR system in conjunction with the restriction endonuclease Bst NI. The activity/thermostability assay on Bst NI and the PCR were performed in the same reactions buffers and subjected to the same thermocycling profile. The results of the two assay were examined to find conditions which allowed both efficient PCR amplification and preservation of restriction endonuclease activity. (Table 6)

TABLE 6

| Basic Buffer | Additional Reagents | PCR Amplification Efficiency | | Bst NI Activity | |
| --- | --- | --- | --- | --- | --- |
| | | 5BKIT 3KiE | 5BKIW 3KiE | 15 cycles | 30 cycles |
| NEB2 | | High | High | Moderate | Low |
| NEB3 | | High | Moderate | Full | Moderate |
| PCR Buffer II | 3 mM $MgCl_2$ | High | High | Moderate | Low |
| | 6 mM $MgCl_2$ | High | High | Moderate | Low |
| | 10 mM $MgCl_2$ | High | High | High | Moderate |
| Stoffel Buffer | 3 mM $MgCl_2$ | High | High | Moderate | Low |
| | 6 mM $MgCl_2$ | High | High | Moderate | Low |
| | 10 mM $MgCl_2$ | Moderate | Moderate | Moderate | Low |
| MTris 10 pH 8.3 | 10 mM $MgCl_2$ | High | High | High | Low |
| HTris 50 pH 8.3 | | Moderate | Moderate | Full | Moderate |
| MTris 10 pH 8.0 | 10 mM $MgCl_2$ | High | Moderate | Moderate | Low |
| MTris 10 pH 8.3 | | High | High | High | Low |
| MTris 10 pH 8.5 | | High | Moderate | Moderate | Low |
| HTris 50 pH 8.0 | 10 mM $MgCl_2$ | Moderate | Moderate | Full | Moderate |
| HTris 50 pH 8.3 | | Moderate | Moderate | Full | Moderate |
| HTris 50 pH 8.5 | | Low | Moderate | Full | Moderate |
| HTris 50 pH 8.3 | 3 mM $MgCl_2$ | High | Moderate | High | Moderate |
| | 6 mM $MgCl_2$ | High | Moderate | Full | Moderate |
| | 10 mM $MgCl_2$ | Moderate | Moderate | Full | Moderate |

TABLE 6-continued

| | | PCR Amplification Efficiency | | Bst NI Activity | |
|---|---|---|---|---|---|
| | | 5BKIT | 5BKIW | | |
| Basic Buffer | Additional Reagents | 3KiE | 3KiE | 15 cycles | 30 cycles |
| HTris 50 pH 8.3 | — | High | Moderate | Full | Moderate |
| 6 mM MgCl$_2$ | DTT | High | Moderate | High | Moderate |
| | aBSA | High | Moderate | High | Moderate |
| | non-a BSA | High | Moderate | High | Moderate |
| | DTT + a BSA | High | Moderate | Moderate | Moderate |
| | DTT + non-a BSA | High | Moderate | Moderate | Low |
| | glycerol | Low | Low | High | Moderate |
| | T4 gene 32 protein | High | Low | Low | Inactive |

The buffer conditions which simultaneously i) resulted in highly efficient amplification with the primer pair 5BKIT and 3KiE and moderately efficient amplification of the primer pair 5BKIW and 3KiE and ii) preserved full Bst NI activity for at least 15 thermocycles and moderate activity for 30 thermocycles, were selected for use in a REMS-PCR assay which requires concurrent activity for DNA Taq polymerase and Bst NI. Buffer conditions that fit these criteria were 100 mM NaCl, 50 mM Tris HCl pH 8.3 and 6 mM MgCl$_2$.

EXAMPLE 3

REMS-PCR USING BstNI and DNA Taq POLYMERASE: ANALYSIS OF CODON 12 OF THE K-RAS GENE IN A MULTIPLEX SYSTEM INCORPORATION INTERNAL CONTROLS A REMS-PCR protocol was used to detect point mutations at codon 12 of the K-ras oncogene. The human cell lines Calu I [ATCC HTB54] and K562 [ATCC CCL243] were obtained from the American Type Culture Collection. Calu I is a lung adenocarcinoma cell which is heterozygous at K-ras codon 12 having both wild type (GGT) and mutant (TGT) sequences (D. J. Capon 1983 Nature 304, 507–513). K562 is a human leukemic cell line which is wild type at codon 12 of K-ras (R. L. Ward et al. Mol Pathol 1995 48, M273–277). Genomic DNA was extracted from Calu I and K562 by standard techniques (Sambrook et al 1989). DNA samples were amplified by REMS-PCR using primers 5BKIT, 5BKIW, 3MKiC and 3KiE. (Table 7)

erate PCR amplicons which are similarly labelled. The bold type G in the primer 3MKiC is mismatched with the K-ras sequence. This results in the induction of a Bst NI recognition/cleavage site which is internal to the primer and which would be incorporated into any amplicons generated by amplification with this primer and either 5BKIT or 5BKIW.

Genomic DNA from K562, Calu I, and a 1:10 mixture (by weight) of Calu I:K562, was amplified in a multiplex REMS-PCR system. The reactions contained genomic DNA (800 ng), 30 pmole of 5BKIT, 30 pmole of 3KiE, 5 pmole of 5BKIW, 80 pmole of 3MKiC, each dNTP (dATP, dCTP, dTTP, dGTP) at 100 μM, 80 units of Bst NI (10 units/μl, New England Biolabs) and 4 units of Taq DNA polymerase (5 units/μl; AmpliTaq, Perkin Elmer) in 100 mμM NaCl, 50 mM Tris (pH 8.3 and 6 mM MgCl$_2$. The total reaction volumes were 100 μl. Two control reactions contained either Calu I DNA or dH$_2$O (no DNA) in the absence of BstNI. The reactions were placed in a GeneAmp PCR system 9600 (Perkin Elmer), denatured at 94° C. for 3 min and then subjected to 30 cycles of 60° C. for 1 min. followed by 92° C. for 20 sec. Reactions were held at 60° C. for 15 min following thermocycling.

A 25 μl aliquot of each reaction was analysed without subsequent manipulation by electrophoresis on a 5% Nusieve GTG gel (FMC Bioproducts, Rockland, Md.). The gel was photographed using a polaroid land camera. In the control reaction, containing Calu I DNA in the absence of Bst NI, three fragments were clearly visible, a 186 bp fragment comprised of amplicons incorporating primers

TABLE 7

```
Primer  Function               Sequence

5BKIT   Diagnostic primer      TATAAACTTGTGGTAGTTGGACCT(SEQ ID NO:5)

5BKIW   PCR control primer     TTTTGTCGACGAATATGATCC(SEQ ID NO:6)

3MKiC   Bst N1 control primer  CTGTATCAAAGCTTGGTCCTGGACCAG(SEQ ID NO:7)

3KiE    3' primer              CTCATGAAAATGGTCAGAGAAAC(SEQ ID NO:8)
```

The bold type C in the primer 5BKIT is mismatched with respect to the sequence of the K-ras gene. This mismatched base results in the induction of the recognition/cleavage site for Bst NI in K-ras amplicons provided that they are wild type at codon 12. Amplicons containing a mutation at either the first or second nucleotide of codon 12 do not contain the recognition/cleavage sequence for Bst NI. Primers 5BKIT and 5BKIW were biotin-labelled at their 5' ends and gen- 5BKIT and 3KiE, a 156 bp fragment comprised of amplicons incorporating primers 5BKIT and 3MKiC, and a 114 bp fragment comprised of amplicons incorporating primers 5BKIW and 3KiE. A fragment of 85 bp comprised of amplicons incorporating primers 5BKIW and 3MKiC was faintly visible.

In the reactions containing Bst NI, the presence of the 185 bp fragment was diagnostic for the presence of K-ras codon 12 mutations. This fragment was visible in reactions containing Calu I and Calu I:K562 DNA at a ratio of 1:10, but not in reactions containing K562 DNA alone. The 156 bp (and 85 bp) Bst NI control fragments were not visible in any reactions containing Bst NI. This demonstrates that Bst NI can mediate complete inhibition of amplification of a second fragment. Since any 156 bp amplicon would contain a Bst NI site, inhibition of amplification of this fragment is not dependent on the mutational status of codon 12. Absence of restriction endonuclease control fragments allows unambiguous interpretation of negative results. The 114 bp PCR control fragment was visible in all reactions including the reaction containing K562 DNA. This confirms that the conditions of the reactions, including the amount of template DNA, were adequate for amplification by the PCR. The presence of PCR control fragments allows unambiguous interpretation of positive results. No fragments were visible in the reaction containing no template DNA.

EXAMPLE 4

REMS-PCR: LIMIT OF DETECTION OF POINT MUTATIONS

The limits of detection of point mutations using REMS-PCR were assessed by analysing codon 12 of the K-ras gene in samples containing Calu I DNA diluted with Sup T1 DNA. Sup T1 [ATCC CRL 1942] is a leukemia cell line which was obtained from the American Type Culture Collection. Calu I is heterozygous mutant at K-ras codon 12 and Sup T1 is wild type at codon 12 of the K-ras gene. Genomic DNA was extracted from these cell lines by standard techniques (Sambrook et al 1989) and amplified by the REMS-PCR. Calu I DNA was diluted with Sup T1 DNA at a ratio (by weight) of Calu I:Sup T1 of 1:10, $1:10^2$, $1:10^3$, $1:10^4$, $1:10^5$ and $1:10^6$.

The REMS-PCR reactions contained genomic DNA (1 $\mu$g), 30 pmole of 5BKIT, 30 pmole of 3KiE, 5 pmole of 5BKIW, each dNTP (dATP, dCTP, dTTP, dGTP) at 100 mM, and 40 units of Bst NI (10 units/$\mu$l, New England Biolabs) in 100 mM NaCl, 50 mM Tris (pH 8.3) and 5 mM $MgCl_2$. Four units of Taq DNA polymerase (5units/$\mu$l); AmpliTaq, Perkin Elmer) were mixed with TaqStart™ antibody (0.16 $\mu$l in 3.8 $\mu$l of antibody dilution buffer; Clontech) to give a final molar ratio of Taq DNA polymerase. TaqStart™ antibody of 1:5. The Taq DNA polymerase:TaqStart™ antibody mixture was incubated for 15 min at room temperature prior to addition to the PCR mixture. The total reaction volumes were 100 $\mu$l. The reactions were placed in a GeneAmp PCR system 9600 (Perkin Elmer), denatured at 94° C. for 2 min and then subjected to 30 cycles of 60° C. for 1 min followed by 92° C. for 20 sec. Reactions were held at 60° C. for 15 min after thermocycling.

A 28 $\mu$l aliquot of each reaction was analysed without subsequent manipulation by electrophoresis on a 5% Nusieve GTG gel (FMC Bioproducts, Rockland, Md.). The gel was photographed using a polaroid land camera and the Stratagne Eagle Eye II video system. The 185 bp fragment generated by amplification with primers 5BKIT and 3KiE was diagnostic for the presence of a mutation at codon 12. This fragment was visible in reactions containing Calu I:Sup T1 DNA at ratios of 1:10, $1:10^2$ and $1:10^3$ by polaroid photography and Eagle Eye imaging and in the reaction containing a ratio of $1:10^4$ by Eagle Eye imagine. This 185 bp fragment was not visible in the reactions containing Calu I:Sup T1 DNA at ratios of $1:10^5$ and $1:10^6$ nor in the reaction containing Sup T1 only. The 114 bp PCR control fragment generated by amplification with primers 5BKIW and 3KiE fragment was visible in all reactions. This confirms reaction conditions, including the amount of template DNA, were adequate for efficient amplification by the PCR.

The REMS-PCR reactions were also analysed in a colorimetric assay. This assay is similar to that described in Findlay et al (Clin. Chem. 1993 39/9, 1927–1933). PCR amplicons were specifically captured by hybridization to oligonucleotide probes that were covalently attached to latex beads which were applied at discrete locations in Periodontal Surecell blanks. The sequence of the capture oligonucleotides, and the specific PCR amplicons captured, are listed below (Table 8). K-Cap 1 and K-Cap 2 were specifically designed to capture only diagnostic K-ras amplicons which were generated by amplification of mutant templates with the primers 5BKIT and 3KiE. K-Cap 3 is designed to capture amplicons generated by amplification of either mutant and wild type templates with either 5BKIT or 5BKIW and 3KiE. H-Cap 1 captures non-specific amplicons and provides a negative control for non-specific amplification or hybridization.

TABLE 8

| Probe (Function) | Sequence | Sizes of fragments with homology (Primers incorporated) | Type(s) of amplicons captured |
|---|---|---|---|
| K-Cap 1 (Diagnostic) | TAGCTGTATCGTCAAGGCA CTCTT(SEQ ID NO:9) | 185 bp (5BKIT/3KiE) | Mutant only |
| K-Cap 2 (Diagnostic) | AAATGATTCTGAATTAGCT GTATCGTC(SEQ ID NO:10) | 185 bp (5BKIT/3KiE) | Mutant only |
| K-Cap 3 (PCR control) | GCACCAGTAATATGCATAT TAAAACAAG(SEQ ID NO:11) | 185 bp (5BKIT/3KiE) 114 bp (5BKIW/3KiE) | Mutant Wild type |
| H-Cap1 (Negative control) | ACCATCCAGCTGATCCAGA ACCAT(SEQ ID NO:12) | Nil | Non-specific |

Aliquots of the four oligonucleotide latex beads (0.25% in 1.6 $\mu$l of 10 mM Tris 1 mM EDTA pH 7.4) were applied on to the Surecell membrane in discrete spots with all four oligonucleotides in each Surecell well. The oligonucleotide latex beads were allowed to dry for 15 minutes. Aliquots of 30 $\mu$l of each PCR was diluted with 170 $\mu$l of 50 mM KCl, 10 mM Tris (pH 8.3) and 10 mM $MgCl_2$. The solution was denatured at 95° C. for 6 min and applied to the Surecell well. The Surecells were then incubated at 50° C. for 5 min to allow hybridization of PCR amplicons with the capture oligonucleotides. The wells were washed with 300 µl of 50 mM KCl, 10 mM Tris (pH 8.3) and 10 mM $MgCl_2$ at 50° C. The hybridized amplicons were reacted with three drops of a conjugate of streptavidin bound to horseradish peroxidase (EC 1.11.1.7) and incubated at room temperature for 2 min. The wash step was repeated to minimize non-specific interactions. Four drops of Leucodye/$H_2O_2$ were added and the Surecell were incubated at room temperature for 2 min. The immobilized complex served as a catalyst in the oxidative conversion of dye molecules from colourless to blue form. The reaction was stopped with 4 drops of 0.1% $NaN_3$. The resultant coloured spots were scored visually by comparison against a colour chart and rated from 0 (no color) to 10 (dark blue) (Table 9)

TABLE 9

| | Color Score | | | | | | |
|---|---|---|---|---|---|---|---|
| Calu I:Sup T1 DNA | 1:10 | $1:10^2$ | $1:10^3$ | $1:10^4$ | $1:10^5$ | $1:10^6$ | Sup T1 |
| K-Cap 1 (Mutant specific) | 9 | 8 | 4 | 2 | 0 | 0 | 0 |
| K-Cap 2 (Mutant specific) | 9 | 8 | 4 | 2 | 0 | 0 | 0 |
| K-Cap 3 (PCR Control) | 9 | 9 | 9 | 9 | 9 | 9 | 9 |
| H-Cap 1 (Non-specific negative control) | 0 | 0 | 0 | 0 | 0 | 0 | 0 |

The sensitivity of the REMS-PCR protocol allowed detection of selectively amplified mutant sequences of K-ras codon 12 when present in a background of $1:10^3$ to $1:10^4$ wild type sequences when analysed by gel electrophoresis or a colorimetric assay. Wild type K-ras codon 12 sequences were not detected in this REMS-PCR assay. The literature suggests that this level of sensitivity will be adequate for analysis of DNA extracted from clinical specimens including tissue resections and biopsies, cytology samples and body fluids/excretions such as stools, urine and sputum containing small numbers of exfoliate tumour cells.

In a clinical setting, where large numbers of samples are simultaneously analysed, it is desirable that amplification does not commence prematurely as this can cause amplification of non-specific products including primer dimers. Monoclonal antibodies can bind to DNA Taq polymerase, and thus inhibit activity and amplification prior to the first denaturation step. In initial experiments using REMS-PCR, the standard molar ratio of DNA Taq polymerase:TaqStart™ of 1:28, as recommended by Clontech, resulted in a false positive due to amplification of wild type Sup T1 DNA templates. Various molar ratios were tested and it was established that lower molar ratios of DNA Taq polymerase:TaqStart™ antibody such as 1:5 resulted in inhibition of non-specific amplification and primer dimer formation in the absence of false positive results.

EXAMPLE 5

ANALYSIS OF CLINICAL SPECIMENS USING REMS-PCR

Genomic DNA was extracted by standard protocols (Sambrook et al 1989) from normal colon mucosa (NC) and colon adenocarcinomas (CA). Samples were analysed for the presence of K-ras codon 12 mutations by REMS-PCR as outlined in example 4 with the following protocol changes; DNA (0.5 µg) was amplified in the presence of 4 units of Taq DNA polymerase and 80 units of Bst NI. A 30 µl aliquot of each reaction was analysed without subsequent manipulation by electrophoresis on a 5% Nusieve GTG gel (FMC Bioproducts, Rockland, Md.).

The 185 bp fragment generated by amplification with primers 5BKIT and 3KiE was diagnostic for the presence of a mutation at codon 12. This fragment was visable by gel electrophoresis in two reactions containing DNA from adenocarcinoma samples CA7 and CA8. This diagnostic fragment was not visible in two other reactions containing DNA from adenocarcinoma samples CA1 and CA2, nor in four reactions containing DNA extracted from normal codon mucosa; NC1, NC2, NC7 and NC8. The 114 bp control fragment generated by amplification with primers 5BKIW and 3KiE was visible in all reactions, indicating efficient PCR amplification had occurred in all reactions.

Genomic DNA from colon tissues had previously been analysed for the presence of mutations at K-ras codon 12 by standard enriched PCR (R. L. Ward et al Mol Pathol 1995, 48, M273–277). Identical results were obtained when amplification was performed by either REMS-PCR or enriched PCR followed by analysis by gel electrophoresis. Both protocols indicated that DNA from adenocarcinoma samples CA7 and CA8 harboured mutations at K-ras codon 12 whereas the DNA from adenocarcinomas CA1 and CA2, as well as normal mucosa samples NC1, NC2, NC3 and NC4, were wild type at codon 12. These results demonstrate that REMS-PCR is suitable for rapid analysis of clinical specimens.

EXAMPLE 6

REMS-PCR: A SYSTEM WHICH ALLOWS IDENTIFICATION OF THE SPECIFIC NUCLEOTIDE SUBSTITUTION

A REMS-PCR system was used to detect point mutations at codon 12 of the K-ras oncogene. Additional analysis with restriction endonucleases both confirmed the diagnosis of a mutation at codon 12 and allowed identification of the specific nucleotide substitution. The human cell lines Calu I [ATCC HTB54], A549 [ATCC], K562[ATCC CCL243], Sup T1 ([ATCC CRL 1942] and were obtained from the American Type Culture Collection. Calu I is a lung adenocarcinoma cell which is heterozygous at K-ras codon 12 having both wild type (GGT) and mutant (TGT) sequences (D. J. Capon 1983 Nature 304, 507–513). A549 is lung adenocarcinoma cell which is homozygous mutant (AGT) at K-ras codon 12 (D. M. Valenzuela and J. Groffen 1986 NAR 14, 843–852). K562 and Sup T1 are leukemic cell lines which are wild type at codon 12 of K-ras. Genomic DNA was extracted from these cell lines by standard techniques (Sambrook et al 1989).

REMS-PCR was performed with primers 5BKIT and 3AKIP which simultaneously induce multiple restriction endonuclease recognition/cleavage sites. Primers 5BK5 and 3K6 function as PCR control primers. (Table 10)

TABLE 10

Sequence: Bases mismatched with the K-ras gene which result in induction of restriction sites are indicated in bold type. (Additional mismatched bases are Primer underlined)

5BKIT TATAAACTTGTGGTAGTTGGACCT(SEQ ID NO:13)

3AKIP GGATGACTCATTAAGGCACTCTTGCCTACGCCC(SEQ ID NO:14)

TABLE 10-continued

| Primer | Sequence: Bases mismatched with the K-ras gene which result in induction of restriction sites are indicated in bold type. (Additional mismatched bases are underlined) |
|---|---|
| 5BK5 | TCAGCAAAGACAAGACAGGTA(SEQ ID NO:15) |
| 3K6 | AGCAATGCCCTCTCAAGA(SEQ ID NO:16) |

The primer 5BKIT results in induction of a Bst NI recognition/cleavage site in K-ras amplicons which are wild type at codon 12. The primer 3 AKIP induces one or more recognition/cleavage site(s) for the group of restriction endonucleases Bsa JI, Sty I, Avr II, Mnl I, Aci I, Rle I and Bsu 36I, in K-ras amplicons which are mutated at codon 12 as indicated below (Table 11).

TABLE 11

K-ras sequences and induced restriction endonuclease recognition/cleavage sites. (Mismatched bases introduced by 5BKIT (C) and 3AKIP (G) are indicated in bold type: Point mutations at codon 12 are underlined; N = T or A or C or G)

|  | Codon 11 | Codon 12 | Codon 13 | Restriction Endonuclease(s) |
|---|---|---|---|---|
| Wild Type | CCT | GGG | GGC |  |
| sequence | CCT | GG |  | Bst N1 |
| Mutant | CCN | NGG |  | Bsa JI |
| sequences | CCT | TGG |  | Sty I |
|  | CCT | AGG |  | Avr 1I/Sty I |
|  | CCT | C |  | Mnl I |
|  |  | GCG | G | Aci I |
|  | T | GTG | GG | Rle AI |
|  | CCT | NAG | G | Bsu 36I |
|  |  | GAG | G | Mnl I |

The expected pattern of sensitivity and resistance of mutant amplicons to cleavage with the group of restriction endonucleases Bsa JI, Sty I, Avr II, Mnl I, Aci I, Rle I and Bsu 36I depends upon the exact mutation present at codon 12 and is indicated in Table 12.

TABLE 12

| Codon 12 positions 1 and 2 (Point mutations are underlined; N = T or A or C) | Restriction endonucleases which cleave mutant amplicons | Restriction endonucleases which do not cleave mutant amplicons |
|---|---|---|
| NG | Bsa JI |  |
| TG | Bsa JI/Sty I | Avr II |
| AG | Bsa JI/Sty I/Avr II |  |
| CG | Bsa JI/Mnl I | Bsu 36I |
| GN |  | Bsa JI |
| GT | Rle AI | Bsa JI |
| GC | Aci I | Bsa JI |
| GA | Mnl I/Bsu 36I | Bsa JI |

Genomic DNA from the human cell lines Calu I, A549, K562 and Sup T1 was amplified in a multiplex REMS-PCR system. The reactions contained genomic DNA (500 ng), 50 pmole of 5BKIT, 50 pmol of 3AKIP, 3 pmole of 5BK5, 3 pmole of 3K6, each dNTP (dATP, dTTP, dGTP) at 100 mM, 40 units of Bst NI (10 units/µl, New England Biolabs) in 100 mM NaCl, 50 mM Tris (pH 8.3) and 6 mM MgCl$_2$. Four units of Taq DNA polymerase (5 units/µl; AmpliTaq, Perkin Elmer) were mixed with TaqStart™ antibody (0.06 µl in 1.5 µl of antibody dilution buffer, Clontech) to give a final molar ratio of Taq DNA polymerase:TaqStart™ antibody of 1:2. The Taq DNA polymerase:TaqStart™ antibody mixture was incubated for 15 min at room temperature prior to addition to the reactions. The total reaction volumes were 100 µl. The reactions were placed in a GeneAmp PCR system 9600 (Perkin Elmer), denatured at 94° C. for 3 min and then subjected to 30 cycles of 60° C. for 1 min followed by 92° C. for 20 sec. Reactions were held at 60° C. for 15 min after thermocycling.

A 20 µl aliquot of each reaction was analysed without subsequent manipulation by electrophoresis on a 5% Nusieve GTG gel (FMC Bioproducts, Rockland, Md.). The gel was photographed using a polaroid land camera. A 58 bp fragment, generated by amplification with primers 5BKIT and 3AKIP, was diagnostic for the presence of a mutation at codon 12. This fragment was visible in reactions containing Calu I and A549 DNA but not visible in reactions containing Sup T1 or K562 DNA. A 167 bp PCR control fragment, generated by amplification with primers 5BK5 and 3K6 was present in all reactions, including reactions containing Sup T1 and K562 DNA. This confirmed that efficient PCR amplification had occurred in all reactions.

A 15 µl aliquot of the reactions containing Calu I or A549 DNA was digested with 10 units of the restriction endonucleases from the group Bsa JI, Sty I, Avr II, Mnl I, Aci I (as indicated below in Table 13) and incubated at the optimum temperature for digestion as specified by the manufacturer (New England Biolabs). The reactions were analysed by electrophoresis on a 5% Nusieve GTG gel (FMC Bioproducts, Rockland, Md.) and the gel was photographed using a polaroid land camera.

TABLE 13

| Template DNA | Primers which generated amplicons | Restriction Endonuclease | Result | Sequence at codon 12 positions 1 and 2 (N = A, C or T) |
|---|---|---|---|---|
| K562 | 5K5/3K6 only | — | — | Wild type - GG |
| Sup T1 | 5K5/3K6 only | — | — | Wild type - GG |
| Calu I | 5BKIT/3AKIP5K |  |  | Mutant |
|  | 5/3K6 | Bsa JI | cleaves | NG |
|  |  | Sty I | cleaves | TG or AG |
|  |  | Avr II | resistant | not AG |
|  |  |  |  | Result: Mutant (TG) |

TABLE 13-continued

| Template DNA | Primers which generated amplicons | Restriction Endonuclease | Result | Sequence at codon 12 positions 1 and 2 (N = A, C or T) |
|---|---|---|---|---|
| A549 | 5BKIT/3AKIP 5K5/3K6 | Bsa JI | cleaves | Mutant NG |
| | | Sty I | cleaves | AG or TG |
| | | Avr II | cleaves | AG |
| | | | | Result: Mutant (AG) |

This REMS-PCR system allows detection of mutations at codon 12 of the K-ras oncogene. Subsequent analysis by restriction endonucleases confirms the presence of the mutation and allows identification of the specific nucleotide substitution.

EXAMPLE 7

REMS-PCR SYSTEM USING Bst NI AND STOFFEL POLYMERASE

Genomic DNA from the human cell lines Calu I ([ATCC HTB54] and Sup T1 [ATCC CRL 1942] was amplified by the REMS-PCR. Genomic DNA was extracted from these cell lines by standard techniques (Sambrook et al 1989). DNA was amplified by REMS-PCR in reactions containing genomic DNA (1 µg), 30 pmole of 5BK1T, 30 pmole of 3KiE, 2 pmole of 5BKIW, each dNTP (dATP, dCTP, dTTP, dGTP) at 100 mM, and 40 units of Bst NI (10 units/µl, New England Biolabs) in 10 mM KCl, 10 mM Tris (pH 8.3) and 10 mM MgCl$_2$ (1×Stoffel buffer; Perkin Elmer) A control reaction contained no DNA (dH$_2$O). Five units of Stoffel fragment (10) units/µl; Perkin Elmer) were mixed with Taq antibody TP4 (D. J. Sharkey et al 1994 Bio/technology 12, 506–509) (0.05 µl in 1.2 µl of Clontech antibody dilution buffer) to give a final molar ratio of Stoffel fragment: Taq antibody TP4 of 1:2. The Stoffel fragment:Taq antibody mixture was incubated for 15 min at room temperature prior to addition to the reactions. The total reaction volumes were 100 µl. The reactions were placed in a GeneAmp PCR system 9600 (Perkin Elmer), denatured at 94° C. for 2 min and then subjected to 30 cycles of 60° C. for 1 min followed by 92° for 20 sec. Reactions were held at 60° C. for 15 min after thermocycling.

A 25 µl aliquot of each reaction was analysed without subsequent manipulation by electrophoresis on a 5% Nusieve GTG gel (FMC Bioproducts, Rockland, Md.). The gel was photographed using a polaroid land camera. The 185 bp fragment generated by amplification with primers 5BKIT and 3KiE was diagnostic for the presence of a mutation at codon 12. This fragment was visible in the reaction containing Calu I DNA, but was not visible in the reaction containing Sup T1 DNA. The 114 bp PCR control fragment, generated by amplification with primers 5BKIW and 3KiE, was visible in both reactions indicating efficient amplification by the PCR. No fragments were visible in the control reaction containing no template.

EXAMPLE 8

REMS-PCR SYSTEM USING Bsl I and Taq DNA POLYMERASE

A REMS-PCR assay was developed to detect point mutations at codon 12 of the K-ras oncogene. In this assay, amplicons contain the recognition/cleavage sequence for the thermophilic restriction endonuclease Bsl I provided they are wild type at codon 12. Amplicons which contain a mutation at either the first or second nucleotide of codon 12 do not contain the recognition/cleavage sequence for Bsl I.

Genomic DNA from the human cell lines Calu I [ATCC HTB54] and K562 [ATC CCL243] was amplified by the REMS-PCR. Calu I is heterozygous mutant at codon 12 of the K-ras gene and K562 is wild type at codon 12. Genomic DNA was extracted from these cell lines by standard techniques (Sambrook et al 1989). Calu I DNA was diluted with K562 DNA at a ratio (by weight) of Calu I:K562 of 1:10, 1:10$^2$ and 1:10$^3$.

DNA was amplified by REMS-PCR using primers 5BKIQ, 5BKIW and 3KiH (Table 14). The 2 bold type C's in 5BKIQ are mismatched with respect to the sequence of the K-ras gene. These mismatched bases cause the induction of a Bsl I site in amplicons which are wild type at codon 12. Primers 5BKIQ and 5BKIW are biotinylated.

TABLE 14

| Primer | Sequence |
|---|---|
| 5BKIQ | TATAAACTTGTGGTACCTGGAGC(SEQ ID NO:17) |
| 5BKIW | TTTTGTCGACGAATATGATCC(SEQ ID NO:18) |
| 3KiH | GAAAATGGTCAGAGAAACC(SEQ ID NO:19) |

The reactions contained genomic DNA (500 ng), 30 pmole of 5BKIQ, 15 pmole of 3KiH, 0.5 pmole of 5BKIW, each dNTP (dATP, dCTP, dTTP, dGTP) at 100 Tris (pH 8.5), 1 mM DTT and 6 mM MgCl$_2$. Eight units of Taq DNA polymerase (5 units/µl; AmpliTaq, Perking Elmer) were mixed with TaqStart™ antibody (0.16 µl in 3.8 µl of antibody dilution buffer, Clontech) to give a final molar ratio of Taq DNA polymerase:TaqStart™ antibody of 1:5. The Taq DNA polymerase:TaqStart™ antibody mixture was incubated for 15 min at room temperature prior to addition to the reactions. The total reaction volumes were 50 µl. The reactions were placed in a GeneAmp PCR system 9600 (Perkin Elmer) and denatured at 94° C. for 2 min. The reactions were then subjected to 10 cycles of 63° C. for 30 sec followed by 92° C. for 20 sec and then 20 cycles of 55° C. for 1 min followed by 92° C. for 20 sec. Reactions were held at 55° C. for 15 min following thermocycling.

A 28 µl aliquot of each reaction was analysed without subsequent manipulation by electrophoresis on a 5% Nusieve GTG gel (FMC Bioproducts, Rockland, Md.). The gel was photographed using a polaroid land camera. The 180 bp fragment generated by amplification with primers 5BKIQ and 3KiH was diagnostic for the presence of a mutation of codon 12. This fragment was visible in reactions containing Calu I:K562 at a ratio of 1:10 and 1:10$^2$. This 180 bp diagnostic fragment was not visible in the reactions containing Calu I:Sup T1 at a ration 1:10$^3$ or in the reactions containing K562 only. The 109 bp PCR control fragment, generated by amplification with primers 5BKIW and 3KiH, was visible in all reactions indicating efficient amplification by the PCR.

This system utilized the restriction endonuclease Bsl I for detection of mutations at K-ras codon 12. This restriction endonuclease could be used in systems for the detection of mutations that occur at either codons 12 or 13 of any of the three ras oncogenes, K-ras, H-ras and N-ras. It could also be used for analysis of other mutations that occur in codons encoding either glycine or proline and for other mutations that occur at the nucleotides C or G.

EXAMPLE 9

ANALYSIS OF K-ras CODON 12 BY A REMS-PCR PROTOCOL WHICH REQUIRES SUBSEQUENT DIGESTION WITH Bst NI.

An alternative protocol was used to detect point mutations at codon 12 of the K-ras oncogene. Genomic DNA was extracted from Calu I [ATCC HTB54] and K562 [ATCC CCL243] by standard techniques (Sambrook et al 1989). Calu I DNA was diluted with K562 DNA at a ratio (by weight) of Calu I:K562 of 1:10, $1:10^2$, $1:10^3$ and $1:10^4$. DNA samples were amplified using primers 5BKIM which has the sequence GACTGAATATAAACTTGTGGTAGT-TGGACCT (SEQ ID NO:20), and 3 AKIL, which has the sequence GGATGACTCAT TTTCGTCCACAAAATGATTCTGAATTAG (SEQ ID NO:21). The bold type C in the primer 5BKIM is mismatched with respect to the sequence of the K-ras gene and results in the induction of the recognition/cleavage sit for Bst NI in K-ras amplicons provided that they are wild type at codon 12. Bases within 3 AKIL which are mismatched with K-ras are underlined.

The reactions contained genomic DNA (800 ng), 40 pmole of 5BKIM and 40 pmole of 3 AKIL, each dNTP (dATP, dCTP, dTTP, dGTP) at 100 µM, 10 µl of 10 ×PCR Buffer II (Perkin Elmer), 1.5 mM $MgCl_2$, 80 units of Bst NI (10 units/µl, New England Biolabs) and 2 units of Taq DNA polymerase (5 units/µl; AmpliTaq, Perkin Elmer) in a total reaction volume of 100 µl. The reactions were placed in a GeneAmp PCR system 9600 (Perkin Elmer), denatured at 94° C. for 3 min and then subjected to 40 cycles of 60° C. for 1 min followed by 92° C. for 20 sec. Reactions were held at 60° C. for 15 min following thermocycling.

A 25 µaliquot of each reaction was analysed without subsequent manipulation. A second 25 µl aliquot of each reaction was incubated with 15 units of Bst NI (10 units/µl, New England Biolabs), 100 µg/ml bovine serum albumin (New England Biolabs) and 3.5 µl of 10×NEB2 buffer (New England Biolabs) in a total reaction volume of 35 µl. These reactions were overlayed with 20 µl of mineral oil and incubated overnight at 60° C. All reactions were analysed by electrophoresis on a 5% Nusieve GTG gel (FMC Bioproducts, Rockland, Md.) and photographed using a polaroid land camera.

In all reactions which had not been subjected to digestion with Bst NI following the PCR, a 103 bp fragment generated by amplification with primers 5BKIM and 3AKIL was visible. Following subsequent digestion with Bst NI, this 103 bp fragment was visible only in reactions containing Calu I:K562 DNA at ratios of 1:10, $1:10^2$ and $1:20^3$. The 103 bp fragment was not visible in the reactions containing Calu I:K562 DNA at a ratio of $1:10^4$ nor in the reaction containing K562 DNA alone. A 73 bp fragment, generated by Bst NI digestion of the wild type amplicons, was visible in all reactions. In reactions which were digested with Bst NI following the PCR, the presence of the 103 bp fragment was diagnostic for the presence of a mutation at codon 12 of K-ras.

The sensitivity of this protocol allowed detection of mutation Calu I DNA when present at a ratio of $1:10^5$ Calu I:K562 DNA. Under these reaction conditions, the inclusion of Bst NI in the PCR reaction resulted in preferential amplification (enrichment) of mutant sequences but did not result in complete inhibition of amplification of wild type K562 sequences. The reactions therefore required digestion with Bst NI prior to final analysis. Such protocols are of intermediate simplicity between standard enriched PCR protocols (which require two rounds of PCR plus an intermediate digestion with a restriction endonuclease to enrich for mutant sequences) and standard REMS-PCR protocols (where amplification of wild type sequences is completely inhibited and no subsequent manipulation such as digestion are required prior to analysis).

DISCUSSION

In REMS-PCR protocols the restriction endonuclease and the DNA polymerase must i) function in identical reaction conditions (eg., salt, pH) which must be compatible with the PCR and ii) be sufficiently thermostable in these reaction conditions to retain activity during the thermocycling which is required for the PCR. Some of the restriction endonucleases listed in Table 1, as well as other thermophilic restriction endonucleases, would be suitable for incorporation in REMS-PCR protocols provided buffer conditions can be identified which i) are compatible with restriction endonuclease activity and which maintain endonuclease activity while reactions are thermocycling during PCR and ii) are compatible with simultaneous DNA polymerase activity and which maintain polymerase activity while thermocycling during the PCR.

As little was previously known about the ability of restriction endonuclease to retain activity during the thermocycling required for the PCR, an assay which is simple and easy to conduct was developed to identify candidate thermophilic restriction endonucleases and reaction conditions. In the activity/thermostability assay, enzymatic activity of a restriction endonuclease, in a variety of reaction conditions, can be compared following a defined number of thermocycles. In this assay, reactions are prepared which contain primers, dNTPs, and DNA polymerase in concentrations which are standard for the PCR. The reactions contain no template DNA but include the buffer system, with or without additional reagents, and the restriction endonuclease to be examined. The reactions are placed on a thermocycler, subjected to a high temperature and thermocycled. After a defined number of thermocycles reactions are removed, plasmid DNA is added to the tubes and the reactions are incubated at the optimal temperature for the restriction endonuclease as specified by the manufacturer. The enzymatic activity of the restriction endonuclease can be assessed by the degree of cleavage of the plasmid DNA as visualized by gel electrophoresis.

The activity/thermostability assay identified various restriction endonucleases, including Bst NI, Bst I, Tru 91 and Tsp 509 I, which are sufficiently thermostable under certain buffer conditions to retain moderate or full catalytic activity following the thermocycling which is essential for the PCR. The reaction conditions which were most effective at preserving catalytic activity during thermocycling were identified. The catalytic activity of restriction endonucleases following thermocycling varied depending on the pH and ionic strength of the buffer, the choice and concentration of monovalent cation ($K^+$ or $Na^+$), the concentration of free $Mg^{2+}$, and the presence of other additives including dithiothreitol (DTT). The influence of each of these components can depend on the other components in the buffer.

It is also likely that the enzymatic activity of restriction endonucleases could be preserved by reducing the temperatures and times for DNA denaturation during the PCR. Factors known to influence the melting temperature of duplex DNA molecules include salt concentration, and the presence of reagents such as formamide, dimethyl sulfoxide, glycerol and ethylene glycol. These reagents are compatible with at least some PCR systems. Inclusion of these or other reagents which affect the DNA melting temperatures, may allow the PCR to be performed at decreased denaturation temperatures and/or times. These reagents may also have a direct positive or negative influence on the activity and/or thermostability of the restriction endonuclease (and/or DNA polymerase). The influence on the activity of restriction endonucleases of various thermocycling profiles, in the presence of additional reagents, can be assessed by the thermostability/activity assay described above. Identification of additional thermophilic restriction endonucleases, and reaction conditions which preserve the activity of restriction endonucleases during thermocycling, can be achieved following routine testing using the activity/thermostability without the exercise of inventive skill.

For REMS-PCR, the reaction conditions must not only preserve catalytic activity of the restriction endonucleases but they must also be suitable for the PCR. The buffer conditions must therefore be compatible with activity and thermostability of a DNA polymerase during thermocycling. There are many commercially available DNA polymerases which can be used for the PCR. These vary widely in their general properties, including both the optimal buffer conditions and the range of conditions they can tolerate. Examination of efficiencies of various DNA polymerases in the PCR, under reaction conditions which are known to preserve restriction endonucleases activity, allows identification of compatible DNA polymerase/restriction endonuclease/buffer combinations. A range of reaction conditions which had been demonstrated to maintain activity of restriction endonucleases, were also assessed for their compatibility with the PCR using various sets of primers and various DNA polymerases. The influence of different components of the reaction conditions on the PCR varied for different primer pairs and can depend on the other reaction components. For this reason, specific primers sets which are required for a PCR should be tested in this manner. Conditions for a PCR which are compatible with the concurrent activity of a restriction endonuclease and a DNA polymerase, and which result in efficient amplification with specific primer pairs can be identified following routine testing without the exercise of inventive skill.

REMS-PCR requires that the recognition/cleavage site for the thermophilic restriction endonuclease spans the nucleotide(s) which are to be analysed for genetic variations. This site can either occur naturally or many be induced by primers which contain internal mismatches to the template. When recognition/cleavage sites for restriction endonucleases are induced by primers, the sites lie partially within the primer and partially within the synthesized sequence which lies 3' to the primer in the amplicons. Primers must therefore include any mismatched bases which are required for induction of the restriction endonuclease site, but must not overlap the bases which are to be analysed. Rules for designing PCR primers which contain mismatched bases near the 3' terminus have been established (S. Kwok, et al. 1990. Nucleic Acids Research, 18, 999–10005). While some terminally mismatched primers amplify inefficiently and reduce the yield of specific amplicons by up to 100 fold, the majority will amplify as efficiently as fully matched primers. For example when the terminal 3' base in a primer is G it will extend on templates containing C, T or G, but not A, at the complementary position.

Recognition/cleavage sites can be more easily induced when the restriction endonuclease requires only a short tetranucleotide sequence for recognition (eg Tru 91 or Tsp 509 I) or when they recognise multiple sequences (eg Bst NI). Recognition/cleavage sites for restriction endonucleases which recognise short sequences which are interrupted are particularly amenable to induction. For example, Bsl I recognises the sequences CCNNNNNNNGG (SEQ ID NO:22), where N is any nucleotide. Bst I could be used to analyse mutations occur at codons which encode either glycine (GGN) or proline (CCN). In general, primers designed to induce a Bst I recognition site at these codons could be extended by DNA polymerases since they would not require mismatched bases near the 3' terminus and single or double mismatches located in the middle of a primer sequence are well tolerated and do not usually inhibit PCR amplification.

Furthermore, one skilled in the art could design primers capable of inducing a Bsl I recognition site for analysis of the vast majority (approximately 80%) of mutations that occur at either a G or a C. Mutation of the bases G and C are very common. For example, the percentage of p53 mutations that occur at either G or C residues is at least 77% of mutations in colorectal tumours, 72% of mutations in lung tumours, 74% of mutations in bladder tumours, 61% of mutations in breast tumours and 66% of mutations in brain tumours (M. Hollstein et al 1996 Nucleic Acids Research 24, 141–146). The following table lists all possible combination of sequences surrounding the bases C or G and the terminal bases which would be required for primers to induce CC or GG at these positions as part of the Bsl I site. The template/primer combinations which are predicted to be compatible with PCR are indicated in Table 15.

TABLE 15

| Sequence of the template adjacent to the target base (underlined)<br>N = A,C,G,T<br>X = A,C,T<br>Y = A,G,T | Primer Type<br>Sense<br>(5' primer)<br>Anti-sense<br>(3' primer) | Primer 3' base | Template 3' base | Compatible with PCR |
| --- | --- | --- | --- | --- |
| GG<u>N</u> | Sense | G | C | Yes |
| AG<u>N</u> | Sense | G | T | Yes |
| CG<u>N</u> | Sense | G | G | Yes |
| TG<u>X</u> | Sense | G | A | No |

TABLE 15-continued

| Sequence of the template adjacent to the target base (underlined) N = A,C,G,T X = A,C,T Y = A,G,T | Primer Type Sense (5' primer) Anti-sense (3' primer) | Primer 3' base | Template 3' base | Compatible with PCR |
|---|---|---|---|---|
| NGG | Sense | N = as per template (sense) | N = as per template (anti-sense) | Yes Yes |
| NCC | Anti-sense | G | C | Yes |
| NCT | Anti-sense | G | T | Yes |
| NCG | Anti-sense | G | G | Yes |
| YCA | Anti-sense | G | A | No |
| CCN | Anti-sense | N = as per template (anti-sense) | N = as per template (sense) | Yes |

Examples of either natural or inducible recognition/cleavage sites for thermophilic restriction endonucleases in genes associated with acquired diseases are listed in Table 16. In these examples, restriction endonucleases which would recognize wild type sequences are identified. The list includes restriction endonucleases which are known to be compatible with REMS-PCR and other endonucleases which are potentially compatible with the method. Primers for analysis of these mutations must include the bases which require induction (indicated in bold) but must not overlap the bases which are to be analysed (underlined). Ras proto-oncogenes (K-ras, H-ras and N-ras) are frequently activated in wide variety of human cancers by the acquisition of point mutations at codons 12, 13 and 61. Since codons 12 and 13 of all three ras genes code for glycine, Bsl I could be used for the analysis of the vast majority of ras mutations. A novel point mutation within intron D of H-ras has also been found in bladder carcinomas. Resistance of HIV strains to certain drugs is associated with the acquisition of point mutations.

TABLE 16

| Gene | Disease | Cause | Wild Type Sequence (Bases to be analysed) Restriction endonuclease recognition site and name (Bases requiring induction) |
|---|---|---|---|
| K-ras N-ras H-ras | Cancer | Point mutations codons 12 and 13 eg K-ras codon 12 | GTTGGAGCTGG SEQ ID NO:23 CCNNNNNNNGG SEQ ID NO:22 Bsl I |
| | | eg K-ras codon 13 | GGAGCTGGTGG SEQ ID NO:24 CCNNNNNNNGG SEQ ID NO:22 Bsl I |
| K-ras | Cancer | Point mutations codon 12 | GCTGG CCTGG Bst NI |
| K-ras N-ras H-ras | Cancer | Point mutations codon 61-position 1 eg. H-ras | CCAGGAGGAGT SEQ ID NO:25 CCNNNNNNNGG SEQ ID NO:22 Bsl I |
| H-Ras | Cancer | Point mutations codon 61-position 3 | CGCCGGCCAGG SEQ ID NO:26 CCNNNNNNNGG SEQ ID NO:22 Bsl I |
| H-ras | Cancer | Point mutations codon 61 (except A to T at position 2) | CCAGG CCAGG Bst NI (CCTGG) |
| H-ras | Bladder Cancer | Point mutations Intron D | GTAA TTAA Tru 91 |
| HIV-I | AZT resistance | Point mutations 1. codon 41 | 1. GAAATG AATT Tsp 5091 GCAATG Bsr DI |
| | | 2. codon 70 | 2. AAATGG AATT |
| | | 3. codon 215 | 3. TTTACC |

TABLE 16-continued

| Gene | Disease | Cause | Wild Type Sequence (Bases to be analysed) Restriction endonuclease recognition site and name (Bases requiring induction) | |
|---|---|---|---|---|
| ddl resistance | Point mutation codon 74 | | TT<u>AA</u><br>AAAA<u>TT</u>A<br>AA<u>TT</u> | Tru 91<br><br>Tsp 5091 |

A selection of genes which can harbour inheritable mutations associated with disease are listed in Table 17. The sequences listed are either wild type or mutant and the positions of potential sequence variations are underlined. Analysis of recessive mutations requires discrimination between heterozygous carriers and homozygous individuals with the latter at risk of disease development. For all of the following examples, restriction endonuclease which would recognize the wild type sequences are identified. For the cystic fibrosis transmembrane conductance gene, restriction endonucleases which recognize the mutated sequence have also been identified.

TABLE 17

| Gene | Disease | Sequence to be analysed | Type of Sequence/Sequence (Bases to be analysed) Endonuclease sites and names (Bases requiring induction) | | |
|---|---|---|---|---|---|
| Cystic fibrosis transmembrane conductance regulator | Cystic fibrosis | Point mutations at<br>1. codon 542 | Wild type sequence<br>1. ATAGTTCTT<u>GG</u><br>CCNNNNNNN<u>GG</u><br>CCT<u>GG</u> | SEQ ID NO:27<br>SEQ ID NO:22<br>Bst NI | Bsl I |
| | | | 2. CTGAGTGGAGGT-<br>CASEQ ID NO:28 | | |
| | | 2. codon 551 | CCNNNNNNN<u>GG</u><br><u>GG</u>TCC | SEQ ID NO:22<br>Bsi ZI | Bsl I |
| | | 3. IVS-4 | 3. TTATAAGAAG<u>G</u><br>CCNNNNNNN<u>GG</u> | SEQ ID NO:29<br>SEQ ID NO:22 | Bsl I |
| | | 4. Deletion codon 508 (3 bp) | 4. AAATATCAT<u>CTT</u><br>GATNNNNAT<u>C</u> | SEQ ID NO:30<br>Bsa BI<br>Bsi BI | |
| | | Wild type sequences<br>1. codon 542 | Mutant sequence<br>1. TCTT<u>T</u>GA<br><u>T</u>TAA | Tru 91 | |
| | | 2. codon 551 | 2. G<u>A</u>TCAACGAG<br>G<u>A</u>TNNNNATC | Bsa BI<br>Bsi BI | |
| | | 3. IVS-4 | 3. AAGAAG<u>T</u>TAA<br><u>T</u>TAA | Tru 9I | |
| | | 4. codon 508 | 4. AAATATCAT<u>TGG</u><br>CCNNNNNNN<u>GG</u> | SEQ ID NO:31<br>SEQ ID NO:22 | Bsl I |
| α-antitrypsin | Emphysema Liver cirrhosis | point mutation codon 342 | Wild type sequence<br>GACCATCGAC<u>G</u><br><br>CCNNNNNNN<u>GG</u> | SEQ ID NO:32<br><br>SEQ ID NO:22 | Bsl I |
| β-globin | β-Thalassemia | Point mutation IVS-1<br>(β⁰-Mediteranean) | Wild type sequence<br>CCCTGGGVAG<u>G</u><br>CCNNNNNNN<u>GG</u> | SEQ ID NO:33<br>SEQ ID NO:22 | Bsl I |
| | | Point mutation poly A signal (β⁺-Black) | Wild type sequence<br>AA<u>T</u>AAA<br>T<u>T</u>AA | Tri 9I | |

Little was previously known about the effect of including a thermostable restriction endonuclease in a PCR. It was discovered that simultaneous activity of a restriction endonuclease and a DNA polymer during the PCR can result in (i) inhibition of amplification of a sequence which contains the recognition/cleavage site for the restriction endonuclease and (ii) selective amplification of a variant of this sequence which lacks the recognition/cleavage site for the restriction endonuclease. This discovery allows the development of protocols known as REMS-PCR. Such protocols could be used for the analysis of acquired or inherited polymorphisms, including point mutations, small deletions and insertions. When protocols for REMS-PCR are designed to detect mutant sequences, the wild type but not mutant sequences contain the recognition/cleavage sequence for a thermophilic restriction endonuclease. amplification of wild type sequences by the PCR is inhibited by the activity of the restriction endonuclease. In contrast, mutant sequences are selectively amplified by DNA polymerase during the PCR.

Protocols for REMS-PCR can also be designed to selectively inhibit amplification of mutant but not wild type sequences. If protocol for REMS-PCR are designed to detect wild type sequences, the mutant but not wild type sequences contain the recognition/cleavage sequence for a thermophilic restriction endonuclease. Amplification of mutant sequences by the PCR would be inhibited by the activity of the restriction endonuclease and wild type sequences would be selectively amplified by the PCR. Failure to amplify specific wild type sequences would be consistent with a homozygous mutation. The ability to detect both wild type and mutant sequences would be consistent with the presence of heterozygous mutation.

Several protocols for REMS-PCR were developed for the analysis of point mutations at codon 12 of the K-ras oncogene. These protocols exploited concurrent enzymatic activity of Bst NI and DNA Taq polymerase, or Bst NI and Stoffel fragment polymerase, or Bsl I and DNA Taq polymerase. These protocols include multiplex primer systems which comprise diagnostic primers and one or two sets of control primers. The diagnostic primers induce a recognition/cleavage site for either Bst NI or Bsl in K-ras amplicons provided positions 1 and 2 of codon 12 are wild type. Inclusion of one of these restriction endonucleases in the PCR results in inhibition of amplification of wild type DNA templates and selective amplification of DNA templates which contain mutations at positions 1 or 2 of codon 12. Amplification with these primers is therefore diagnostic for the presence of a point mutation at codon 12. Additional control primers are included in all reactions to confirm that the reaction conditions, including the amount of template DNA, are adequate for amplification by the PCR. These PCR control primers can flank any region which does not contain the endonuclease recognition/cleavage site. Amplicons incorporating these primers must be present for unambiguous interpretation of negative results. A second control primer was included in one multiplex system to confirm that the restriction endonuclease could mediate complete inhibition of amplification by the PCR. Control primers for the restriction endonuclease must either induce or flank the recognition/cleavage site for the restriction endonuclease used in the REMS-PCR protocol. Absence of amplicons incorporating these primers allows unambiguous interpretation of positive results.

The limits of detection of the REMS-PCR were assayed by analysis of samples containing Calu I DNA (heterozygous mutant at K-ras codon 12) diluted in Sup T1 DNA (wild type at K-ras codon 12) in the presence of Bst NI and DNA Taq polymerase. The detection of diagnostic amplicons indicated the presence of K-ras sequences which were mutated at codon 12. Diagnostic amplicons were visualized, using gel electrophoresis and colorimetric analysis, in samples containing Calu I:Sup T1 at ratios of 1:10 to 1:10,000 but not in samples containing Sup T1 DNA. The literature suggests that this level of sensitivity will be adequate for analysis of DNA extracted from clinical specimens including tissue resections and biopsies, cytology samples and body fluids/excretions such as stools, urine and sputum containing small numbers of exfoliate tumour cells (D. Sidransky et al., 1992, Science 256, 102–1; L Mao et al. 1994 Cancer Res. 54, 1634–1637). The application of REMS-PCR to the analysis of clinical specimens was demonstrated. Mutations at K-ras codon 12 were detected in DNA extracted from two out of four colon adenocarcinomas but none were detected in DNA extracted from four normal colon mucosas.

In an extension of the REMS-PCR, the protocol can be performed with primers which simultaneously induce i) a recognition/cleavage site for a restriction endonuclease that is present only in the wild type sequence and ii) multiple recognition/cleavage sites for restriction endonucleases that are specific for all possible mutated sequences. Subsequent analysis of diagnostic amplicons with the restriction endonuclease allows confirmation of the presence of a mutation in these amplicons and allows identification of the exact nucleotide substitutions in all cases.

It is also possible to develop REMS-PCR systems which result in selective amplification of mutant sequences but which do not result in complete inhibition of amplification of wild type sequences or vice versa. Reactions therefore require digestion with appropriate restriction endonuclease following PCR prior to analysis. Such protocols are of intermediate simplicity between standard enriched PCR protocols and standard REMS-PCR protocols where amplification of wild type sequences is completely inhibited.

REMS-PCR is compatible with a variety of capture and detection systems. This allows automation of the complete protocol and thus rapid analysis of large numbers of samples. Examples of capture systems include but are not restricted to i) PCR primers with a GCN4 recognition tag captured on GCN4 coated plates; ii) biotinylated primers captured with avidin or streptavidin; iii) digoxigenin-labelled products captured using anti-digoxigenin antibodies; and iv) complementary oligonucleotides attached to latex or magnetic beads. Examples of detection systems include, but are not restricted to, i) biotinylated PCR primers visualized with streptavidin/horse radish peroxidase, ii) direct labelling with molecules such fluorescein-isothiocyanate or alkaline phosphatase; and iii) digoxigenin-labelled products detected using anti-digoxigenin antibodies.

REMS-PCR provides a sensitive, rapid method which is suitable for analysis of genetic variations which are associated with disease. The ability to simultaneous sustain the activities of a restriction endonuclease and a DNA polymerase during the PCR allows the development of simple protocols for selective amplification of variant sequences in reactions which contain all reagents, including all enzymes, at the initiation of the PCR. Reactions can be performed in a closed system which reduces the opportunity for contamination during the PCR. The protocol for REMS-PCR has fewer steps than other protocols which utilize restriction endonucleases to mediate selective amplification and/or analysis of mutant sequences. In general, the reactions do not require further manipulation prior to detection, however, the method does not preclude subsequent analysis of diagnostic amplicons for identification of the exact nucleotide substitution. A reduction in the number of steps required for selective amplification and analysis with restriction endonucleases makes the REMS-PCR assay rapid, less labour intensive and more amenable to automation.

It will be appreciated by persons skilled in the art that numerous variations and/or modifications may be made to

References

Capon, D. J., Seeburg, P. H., McGarth, J. P., Hayflick, J. S., Edmun, U., Levinson, A. D. and Goeddel, D. V. (1983) Activation of Ki-ras 2 gene in human colon and lung carcinomas by two different point mutations. Nature 304, 507–513.

Chehab, F. F., Doherty, M., Cai, S., Kan, Y. W., Cooper, S. and Rubin, E. M. (1987) Detection of sickle cell anaemia and thalassaemias. Nature 329, 293–294.

Cohen, J. B. and Levinson A. D. (1988) A point mutation in the last intron responsible for increased expression and transforming activity of the c-Ha-ras oncogene. Nature 334, 119–124.

Kumar R. and Barbacid M. (1988) Oncogene detection at the single cell level. Oncogene 3, 647–651

Kwok, S., Kellogg, D. E., McKinney, N., Spasic, D., Goda, L., Levenson, C., and Sninsky, J. J. (1990) Effect of primer-template mismatches on the polymerase chain reaction: Human immunodeficiency virus type I model studies. Nucleic Acids Research, 18:999–10005).

Levi, S., Urbano-Ispizua, A., Gill, R., Thomas D. M., Gilbertson J., Foster C. and Marshall C. J. (1991) Multiple K-ras codon 12 mutations in cholangiocarcinomas demonstrated with a sensitive polymerase chain reaction technique. Cancer Res. 51, 3497–3502

Mao, L., Hruban R. H., Boyle J. O., Tockman M. and Sidransky D. (1994) Detection of oncogene mutations in sputum precedes diagnosis of lung cancer. Cancer Res. 54, 1634–1637.

Saiki, R. K., Scharf, S., Faloona, F., Mullis, K. B., Horn, G. T., Erlich, H. A. and Arnheim, N. (1985) Enzymatic amplification of β-globin genomic sequences and restriction site analysis for diagnosis of sickle cell anemia Science 230, 1350–1354.

Sambrook, J., Fritsch, E. F. and Maniatis, T. (1989) Molecular Cloning: A Laboratory Manual. 2nd edn. New York: Cold Spring Harbour Laboratory Press.

Sharkey, D. J., Scalice, E. R., Christy, K. G. Jr., Atwood, S. M. and Daiss, J. L. (1994) Antibodies as thermolabile switches: High temperature triggering for the polymerase chain reaction. Bio/technology 12, 506–509.

Sidransky, D., Tokino T., Hamilton S. R., Kinzler K. W., Levin, B., Frost P. and Vogelstein B. (1992) Identification of ras oncogene mutations in the stool of patients with curable colorectal tumors. Science 256, 102–105.

Singh, J., Rao, C. V., Kulkarni N., Simi B. and Reddy B. S. (1994) Molecular markers as intermediate end-points in chemoprevention of colon cancer. Modulation of ras activation by sulindac and phenylhexylisothiocyanate during colon carcinogenesis Int.J.Oncol. 5, 1009–1018.

Todd, A. V., Ireland, C. M. and Iland, H. J. (1991) Allele-specific enrichment: A method for detection of low level N-ras gene mutations in acute myeloid leukemia. Leukemia 5, 160–161.

Valenzuela, D. M. and Groffen J. (1986) Four human carcinoma cell lines with novel mutations in position 12 of the c-K-ras oncogene. Nucleic Acids Research 14, 843–852

Ward, R. L. Santiago, F., Hawkins, N. J., Coomber, D., O'Connor, T. and Todd, A. V. (1995) A rapid PCR ELISA for the detection of activated K-ras in colorectal cancer. J Clin Pathology:Mol Pathol. 48, M273–277.

Patents cited
WO 84/01389 (Weinberg et al. Massachusetts Institute of Technology)
EPO 684 315 AI (Becton Dickinson and Company)
U.S. Pat No. 4,683,202 (Mullis, K. B. Cetus Corporation)
U.S. Pat. No. 4,683,195 (Arnheim, N. et al. Cetus Corporation)
U.S. Pat. No. 4,800,159 (Arnheim, N. et al. Cetus Corporation)
U.S. Pat. No. 4,965,188 (Ehrlich H. A. et al. Cetus Corporation)
U.S. Pat. No. 5,176,995 (Erlich H. A. et al. Hoffmann-LaRoche Inc.)

What is claimed is:

1. A method of detecting a genetic polymorphism in an individual, the method comprising the following steps:
   (1) obtaining a sample containing nucleic acid from the individual;
   (2) amplifying the nucleic acid sample from step (1) by a process involving thermocycling and primers, the amplification occurring in the presence of a thermostable restriction endonuclease which is active during thermocycling, the primers being selected such that they introduce a sequence recognized by the thermostable restriction endonuclease into the nucleic acid resulting from amplification of the sample nucleic acid not including the polymorphism, or from amplification of the sample nucleic acid not including the polymorphism amplified from nucleic acid including the polymorphism, wherein the sample nucleic acid is not amplified prior to step (2) and wherein during thermocycling the thermostable restriction endonuclease inhibits amplification of the nucleic acid which contains the sequence recognized by the restriction endonuclease and allows amplification of the nucleic acid which lacks the sequence recognized by the restriction endonuclease; and
   (3) analyzing the product of step (2) to determine the presence or absence of the polymorphism.

2. A method as claimed in claim 1 in which the primers introduce the sequence recognised by the thermostable restriction endonuclease into the nucleic acid resulting from amplification of the sample nucleic acid not including the polymorphism.

3. A method of detecting a genetic polymorphism in an individual, the method comprising the following steps:
   (1) obtaining a sample containing nucleic acid from the individual;
   (2) amplifying the nucleic acid sample from step (1) by a process involving thermocycling and primers, the amplification occurring in the presence of a thermostable restriction endonuclease which is active during thermocycling, the restriction endonuclease being selected such that it recognizes nucleic acid not including the polymorphism but not nucleic acid including the polymorphism or vice versa, wherein the sample nucleic acid is not amplified prior to step (2) and wherein during thermocycling the thermostable restriction endonuclease inhibits amplification of the nucleic acid which contains the sequence recognized by the restriction endonuclease and allows amplification of the nucleic acid which lacks the sequence recognized by the restriction endonuclease; and
   (3) analyzing the product of step (2) to determine the presence or absence of the polymorphism.

4. A method as claimed in claim 3 in which the thermostable restriction endonuclease recognises nucleic acid not including the polymorphism.

5. A method as claimed in claim 2 in which the method further comprises the following additional steps of:
   (4) adding to the amplified nucleic acid from step (2) at least one additional restriction endonuclease, the at least one restriction endonuclease being selected such that it digest the amplified nucleic acid resulting from amplification of the sample nucleic acid which includes a particular polymorphism; and
   (5) determining whether digestion occurs in step (4), digestion being indicative of the presence of the particular polymorphism.

6. A method as claimed in claim 1 in which the process involving thermocycling is PCR.

7. A method as claimed in claim 1 in which the step (3) analysis comprises detecting the presence or absence of amplified nucleic acid from step (2), the presence or absence of amplified nucleic acid indicating the presence or absence of the polymorphism.

8. A method as claimed in claim 1 in which the nucleic acid is DNA.

9. A method as claimed in claim 1 in which the thermostable restriction endonuclease is selected from the group consisting of Bst NI, Bsl I, Tru 9I and Tsp 509 I.

10. A method as claimed in claim 1 in which the genetic polymorphism is detected in one of the ras proto-oncogenes, K-ras, N-ras, and H-ras, or the p53 tumour suppressor gene.

11. A method as claimed in claim 10 in which the genetic polymorphism is detected in codon 12 of K-ras.

12. A method as claimed in claim 1 in which the genetic polymorphism is detected in HIV-I, cystic fibrosis transmembrane conductance regulator, α-antitrypsin or β-globin.

13. A method as claimed in claim 4 in which the method further comprises the following additional step of:
   (4) reacting the amplified nucleic acid from step (2) with at least one restriction endonuclease, the at least one endonuclease being selected such that it digests the amplified nucleic acid at a particular polymorphism; and (5) determining whether digestion occurs in step (4), digestion being indicative of the presence of the particular polymorphism.

14. A method as claimed in claim 3 in which the process involving thermocycling is PCR.

15. A method as claimed in claim 3 in which the step (3) analysis comprises detecting the presence or absence of amplified nucleic acid from step (2), the presence or absence of amplified nucleic acid indicating the presence or absence of the polymorphism.

16. A method as claimed in claim 3 in which the nucleic acid is DNA.

17. A method as claimed in claim 3 in which the thermostable restriction endonuclease is selected from the group consisting of Bst NI, Bsl I, Tru 9I and Tsp 509 I.

18. A method as claimed in claim 3 in which the genetic polymorphism is detected in one of the ras proto-oncogenes, K-ras, N-ras, and H-ras, or the p53 tumor suppressor gene.

19. A method as claimed in claim 18 in which the genetic polymorphism is detected in codon 12 of K-ras.

20. A method as claimed in claim 3 in which the genetic polymorphism is detected in HIV-I, cystic fibrosis transmembrane conductance regulator, α-antitrypsin or β-globin.

21. The method according to claim 9, wherein the restriction endonuclease is BstNI and the amplification of the nucleic acid occurs in the presence of a buffer comprising 50 or 100 mM NaCl and 3, 6, or 10 mM $MgCl_2$.

22. The method according to claim 21, wherein the NaCl concentration is 100 mM.

23. The method according to claim 9, wherein the restriction endonuclease is BstNI and the amplification of nucleic acid occurs in the presence of a buffer including DTT.

24. The method as claimed in claim 4 wherein the restriction endonuclease is Bst NI and the amplification of the nuclease acid occurs in the presence of a buffer including from 50 mM to 100 mM NaCl and from 3 mM to 10 mM $MgCl_2$.

25. The method as claimed in claim 24 wherein the NaCl concentration is 100 mM.

26. The method as claimed in claim 9 wherein the restriction endonuclease is BslI and the amplification of the nucleic acid occurs in the presence of a buffer including DTT.

* * * * *